US008661687B2

(12) United States Patent
Rebaudieres et al.

(10) Patent No.: US 8,661,687 B2
(45) Date of Patent: Mar. 4, 2014

(54) BLADE SHAVING DEVICE AND METHOD

(75) Inventors: Jean Rebaudieres, Compiegne (FR); Jérôme Buscail, Le Chesnay (FR)

(73) Assignee: Societe BIC, Clichy (FR)

( * ) Notice: Subject to any disclaimer, the term of this patent is extended or adjusted under 35 U.S.C. 154(b) by 597 days.

(21) Appl. No.: 12/442,452

(22) PCT Filed: Sep. 20, 2007

(86) PCT No.: PCT/FR2007/051984

§ 371 (c)(1), (2), (4) Date: Mar. 23, 2009

(87) PCT Pub. No.: WO2008/035017

PCT Pub. Date: Mar. 27, 2008

(65) Prior Publication Data

US 2010/0024615 A1 Feb. 4, 2010

(30) Foreign Application Priority Data

Sep. 21, 2006 (FR) ..................................... 06 08292

(51) Int. Cl.

| | |
|---|---|
| ***B26B 19/00*** | (2006.01) |
| ***A61B 18/18*** | (2006.01) |
| ***B26B 21/00*** | (2006.01) |

(52) U.S. Cl.
USPC ..................... 30/34.05; 606/43; 30/32; 30/50

(58) Field of Classification Search
USPC ............. 30/32, 34.05, 45, 342, 77, 50; 83/34; 606/131, 132, 133, 167, 172, 36, 43
See application file for complete search history.

(56) References Cited

U.S. PATENT DOCUMENTS

| | | | | |
|---|---|---|---|---|
| 1,505,578 | A | 8/1924 | Barra | |
| 1,552,026 | A | 9/1925 | Barra | |
| 4,380,121 | A * | 4/1983 | Naimer et al. | 30/42 |
| 4,914,817 | A * | 4/1990 | Galligan et al. | 30/77 |
| 5,026,369 | A * | 6/1991 | Cole | 606/36 |
| 5,165,170 | A | 11/1992 | Sagol et al. | |
| 5,419,344 | A * | 5/1995 | DeWitt | 128/898 |
| 5,797,926 | A | 8/1998 | Mehl, Sr. | |
| 5,846,252 | A * | 12/1998 | Mehl, Sr. | 606/133 |
| 5,868,738 | A * | 2/1999 | Mehl, Sr. | 606/36 |
| 6,014,918 | A * | 1/2000 | Orloff | 83/13 |
| 6,039,746 | A * | 3/2000 | Cole et al. | 606/133 |
| 6,063,076 | A * | 5/2000 | Mehl et al. | 606/36 |
| 6,817,101 | B1 * | 11/2004 | Bohmer | 30/34.05 |
| 6,836,966 | B2 * | 1/2005 | Patrick | 30/34.05 |
| 7,170,034 | B2 * | 1/2007 | Shalev et al. | 219/223 |
| 7,996,994 | B2 * | 8/2011 | Trezon | 30/34.05 |

(Continued)

FOREIGN PATENT DOCUMENTS

| | | |
|---|---|---|
| WO | WO 2004/008907 | 1/2004 |
| WO | WO 2006/100383 A1 | 9/2006 |

*Primary Examiner* — Kenneth E. Peterson
*Assistant Examiner* — Samuel A Davies
(74) *Attorney, Agent, or Firm* — Jones Day

(57) ABSTRACT

A shaving device that includes a shaving head intended to be moved in contact with the skin, where the head has at least one blade made of conducting material having a cutting edge suitable for cutting hairs. The blade is supplied electrically by a current source suitable for transmitting a current generating an electrolysis effect at the root of a hair. A shaving method employing current transmission by the blade is also described.

9 Claims, 2 Drawing Sheets

(56) References Cited

U.S. PATENT DOCUMENTS

2005/0172489 A1* 8/2005 Aviza ................................ 30/32
2006/0032054 A1* 2/2006 Simms et al. ................ 30/34.05
2006/0242848 A1* 11/2006 Ciccone .......................... 30/539
2008/0189953 A1* 8/2008 Jessemey et al. ................. 30/45
2009/0000123 A1 1/2009 Trezon
2011/0214290 A1* 9/2011 Micinilio et al. ................. 30/32

* cited by examiner

BLADE SHAVING DEVICE AND METHOD

CROSS REFERENCE OF RELATED APPLICATION

This application is a national stage application of International Application No. PCT/FR2007/051984, filed on Sep. 20, 2007, which claims the benefit of French Patent Application No. 06 08292 filed on Sep. 21, 2006, the entire contents of both applications being incorporated herein by reference.

BACKGROUND OF INVENTION

Field of Invention

Embodiments of the present invention relate to shaving devices having a shaving head intended to be moved in contact with the skin, said head comprising at least one blade made of conducting material having a cutting edge suitable for cutting hairs.

Devices of this type are well known, such as for example wet shavers generally comprising several blades in the form of thin metal plates mounted into an overmolded plastic support.

These devices allow rapid and very close shaving, in particular thanks to the advances in the technology of shaving blades. However, for some users, the hairs grow back quickly and the quality of the esthetic result obtained disappears only after a few hours. There is therefore a need for a shaving device that provides a more lasting esthetic result.

Moreover, hair removal devices exist that remove the root of the hairs and therefore provide a lasting result. Among these hair removal devices there are especially devices that transmit an electric current to the root of the hairs in order to produce an electrolysis effect that destroys the hair bulb and causes the hair to drop off.

It should be recalled here that the electrolysis effect applied to the hair is known per se, as for example indicated in document U.S. Pat. No. 5,026,369-B1. At the hair follicle, there is a saline aqueous medium (NaCl+H2O) that can undergo the electrolysis process. Subjecting this medium to an electrolysis electric current causes ionization, with formation of the compound NaOH. The sodium hydroxide thus formed is corrosive with respect to the follicle of the hair and thus destroys the latter. The hair removal devices of this type must transmit a DC current of negative polarity to the hair root in order to form the compound NaOH. This is because applying an AC current or changing to a positive electrode would result in the decomposition of the NaOH compound that was formed.

However, these hair removal devices have the drawback of requiring the electric current to be applied for a rather long time, several tens of seconds, to the region to be treated and may be painful when it is desired to increase the voltage and the intensity of the current transmitted, owing to the presence of nerve receptors in the epidermis. This is because, in such devices, the current is mainly transmitted from the surface of the skin to the roots of the hairs through the epidermis, given that the hairs prove to be poor electrical conductors. Various cream compositions and various materials have been proposed for these hair removal devices, in order to improve the transmission of the current to the hair roots.

However, hitherto only devices using a negative electrode in the form of a needle intended to be inserted at the root have shown to be satisfactorily effective.

The problem of pain is tackled independently in document U.S. Pat. No. 6,014,918-B1, which proposes a shaver in which the head contains several closely spaced electrodes in order to provide transcutaneous electric nerve stimulation. This nerve stimulation has the effect of reducing the sensation usually felt during shaving. However, the nerve stimulation using electrical pulses is unsuitable for achieving hair removal through electrolysis forming the ionic compound NaOH at the hair root.

There is therefore a need to improve the conduction of current to the hair root, in particular so as to reduce the electrolysis current application time and/or to limit the sensations of pain that may be generated by this current.

For this purpose, one subject of the present invention is a shaving device of the aforementioned type, characterized in that said at least one blade is supplied electrically by a current source suitable for transmitting a current generating an electrolysis effect at the root of a hair, at least while said hair is being cut by said blade.

It has been found that with such a device satisfactory conduction of the current to the roots of the hairs is achieved, despite the somewhat insulating nature of the latter. This might be explained by the actual structure of a hair and destruction of this structure by the cutting edge of the blade. Specifically, a hair consists on the outside of a relatively insulating sheath—a cuticle—and on the inside a fibrous cortex and a medulla. The cortex is also formed from a relatively insulating material, but one having a structure consisting of linear fibers oriented along the axis of the hair. It is assumed that after the cuticle has been destroyed, the cutting edge of the blade conducts the electricity via the cortex, the anisotropic structure of which promotes transmission of the current to the hair bulb and the hair papillae. Likewise, the central part, called the medulla, which is rich in water, promotes this transmission.

It is thus possible to transmit an electric current generating an electrolysis effect without causing excessive pain, and to do so despite the very short time during which the hair is in contact with the blade, is pulled from its root and finally cut off. Of course, this electrolysis effect is too short to destroy the hair bulb and cause the hair root to drop out after a single shaving operation. However, it turns out that a single shaving operation is sufficient to cause deterioration in the hair bulb and/or follicle, which, upon being repeated, for example when shaving daily, is sufficient to very greatly slow down the rate of hair regrowth and to make the esthetic result obtained longer lasting. The shaving device according to the invention, although of a very different nature from a hair removal device, does allow the esthetic result obtained to last substantially longer.

SUMMARY OF THE INVENTION

In preferred embodiments, one or other of the following arrangements may furthermore be provided:

- a conducting current return member is designed to come into contact with the user, during shaving, in a region different from the region to be shaved and is connected to the current source in order to provide the current return back to said source;
- the conducting current return member is a gripping member;
- the current return member has an area intended to come into contact with the user that is very much greater than the area of said at least one blade capable of coming into contact with the region to be shaved;
- the current source includes a negative terminal connected to said at least one blade and a positive terminal connected to the conducting current return member;

an additional conducting current transmission member is placed on the shaving head so as to come into contact with the skin, preferably before said at least one blade has passed, and is supplied so as to transmit an electrolysis current to the root of a hair;

the additional current transmission member is a skin-stretching strip placed in front of said at least one blade;

the current source is suitable for transmitting electric currents of different characteristics to said at least one blade and to said additional transmission member;

the electric power transmitted by said at least one blade when cutting a hair is greater than the average power transmitted by the additional transmission member;

the shaving head comprises a plurality of blades, all said blades being electrically supplied in order to transmit an electrolysis current;

the shaving head comprises a plurality of blades, at least one blade, and preferably that placed at the front relative to the direction of shaving, being supplied so as to transmit an electrolysis current; and a skin protection device is placed at least partly on the cutting edge of said at least one blade, said protection device being made of nonconducting material.

The present invention also relates to a shaving method, for which at least one blade having a cutting edge suitable for cutting a hair is provided, in which the shaving operation comprises:

moving the blade along a defined region of the skin;

cutting the hairs present in said defined region by the cutting edge of the blade;

supplying electric current to the blade; and transmitting via said blade an electric current suitable for generating an electrolysis effect at the root of a given hair while this hair is being cut.

BRIEF DESCRIPTION OF THE DRAWINGS

Other features and advantages of the invention will become apparent from the following description given by way of non-limiting example, and with reference to the figures in which.

DESCRIPTION

Figure 1:
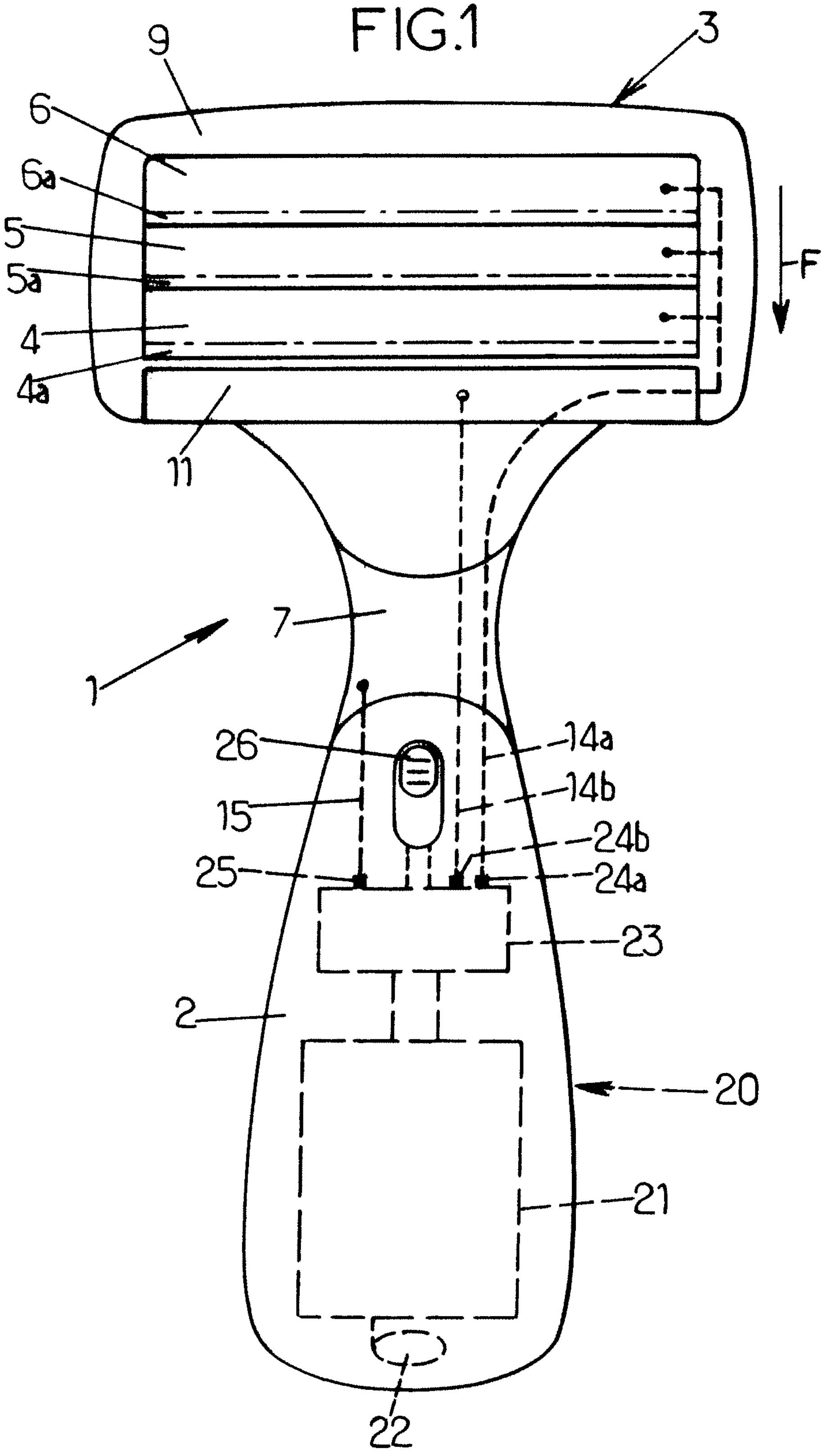
FIG. 1 is a schematic front view of a shaving device according to the invention comprising a shaving head mounted with blades.

FIG. 1 shows a shaving device 1 comprising a casing 2, which forms a handle, and a shaving head 3 comprising three blades (4, 5, 6) made of metal or of any other material that is a good electrical conductor.

The blades are mounted in a frame 9, for example by overmolding the constituent plastic of this frame onto the blades. However, any known way of mounting the blades may be applied, especially one that allows blades to have a certain mobility.

The blades (4, 5, 6) are arranged parallel to one another so that their cutting edges (4*a*, 5*a*, 6*a*) are flush with the surface of the head 3 and oriented in the same direction F, which defines the direction of shaving for a wet shaver as shown in FIG. 1.

Apart from the blades, the head 3 may include other elements such as for example, in the embodiment shown in FIG. 1, a lubricating strip 11 mounted at the front relative to the shaving direction F. There could be another device, such as for example a stretching strip for stretching the skin before the blades pass over it.

The shaving head 3 may be connected to the casing 2 in any known manner. There may in particular be a removable link, in which case the shaving head 3 forms a disposable cartridge, which is articulated so as to offer greater shaving comfort.

The casing 2 includes an electric current source 20 comprising, in the embodiment shown, a rechargeable battery 21, an electrical energy collection loop 22 and a control module 23 having current output terminals (24*a*, 24*b*) and a return terminal 25. These elements are connected together and to a manual control member 26 formed by a button that can slide on the surface of the casing 2.

The battery 21 is connected to the energy recovery loop 22 so as to recharge the battery through the plastic wall of the casing when the shaving device 1 is placed on a suitable stand.

The control module 23 of the current source 20 is produced here in the form of an electronic chip making it possible not only to supply current to the terminals 24 and 25 when the control button 26 is placed in the operating position, but also to regulate the current and/or the voltage across the terminals of this module. Other functions may be provided by the control module 23, such as for example the lighting of a warning lamp or the processing of data coming from a sensor, in order to regulate or vary the current.

However, the current source 20 could adopt very different forms, provided that it is suitable for delivering a current that meets the abovementioned characteristics. To give an example, the control module 23 could essentially provide a function whereby the voltage is raised by means of a few electronic components and a switch function. The battery could of course be replaced by a cell, but also by a power supply external to the casing, optionally incorporating a regulator and connected to the casing 2 that forms the handle via an electrical lead.

As shown schematically by the broken lines in FIG. 1, a first supply line 14*a* electrically connects the output terminal 24*a* to each of the blades (4, 5, 6) of the shaving head 3. This line could be produced by an electrical wire soldered at each of its ends if the shaving head were to be permanently connected to the casing 2, but in the embodiment shown, the line 14*a* consists in fact of various conducting elements connected together via contacting or interlocking connections, and preferably so that by simply mounting the head 3 on the casing 2 these connections are established. In this embodiment, in which all the blades are electrically supplied via the same line, and therefore with the same current and the same voltage, a metal piece supporting the blades may supply the latter, by being connected to a single point on the line 14*a* and not three separate points, as is shown in the diagram.

A second supply line 14*b* connects the second output terminal 24*b* to the lubricating strip 11, which is of course conducting owing to its chemical composition, and partially soluble in an aqueous medium. Just as in the case of the first conducting line 14*a*, the second conducting line 14*b* is preferably designed to establish a connection when mounting the head 3 on the casing.

Moreover, an electrical line 15 connects the current return terminal of the module 23 to a conducting element 7 which is placed on the surface of the casing 2 in a region where the latter is gripped, so as to be in contact with one's hand during use.

It should be noted that the frame 9 of the shaving head is preferably made of insulating material so that the blades (4, 5, 6) and the lubricating strip 11 supplied via different electrical lines (14*a*, 14*b*, 15) are effectively at different potentials.

Figure 2:
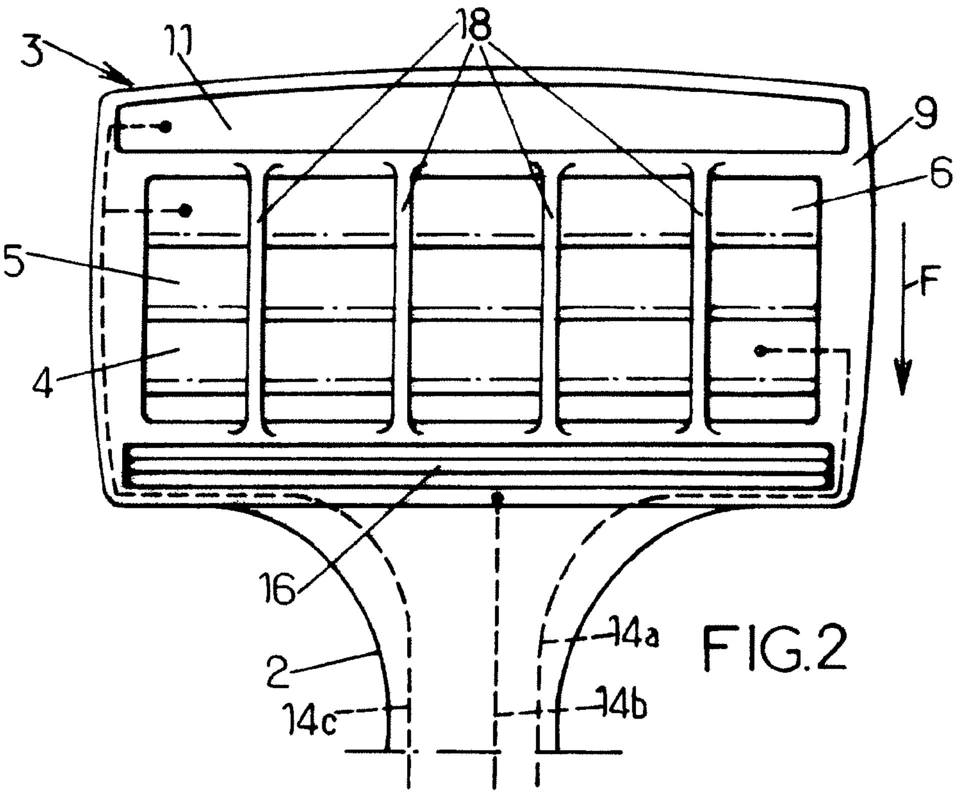
FIG. 2 is a front view of a shaving head according to a second embodiment of the invention.

FIG. 2 shows a second embodiment of the head 3 of the shaving device 1, which includes, as in the first embodiment, three blades (4, 5, 6) arranged in a similar fashion. Three electrical lines (14a, 14b, 14c) arrive in the shaving head 3 and are connected to a current source in a completely similar manner to the first embodiment. It should however be noted that the second electrical line 14b is connected to a stretching strip 16 placed in front of the blades relative to the shaving direction F, as in the case of the lubricating strip 11 of the first embodiment. However, provision must be made for this stretching strip to be conducting, for example by making it from a metal or a filled plastic.

In this second embodiment, the lubricating strip 11 is placed to the rear of the blades relative to the shaving direction F and is connected to a third supply line 14c which makes it possible to deliver an electrolysis current having characteristics that are identical to or different from the first and second lines 14a, 14b.

It should also be noted that only the first blade 4, that is to say the one located at the front relative to the shaving direction F, is electrically supplied by the first line 14a. Since the last blade 6 is electrically connected to the supply line 14c, it is therefore necessary to provide, in this embodiment, electrical isolation at least between the first blade 4 and the last blade 6, or any group of blades supplied by different lines (14a, 14c), given that the shaving head may comprise more than three blades and that several of them may be electrically connected to the same line. The shaving head could have a different number of blades, including a single blade that is electrically supplied.

It will also be seen in this second embodiment that the shaving head 3 includes a protection device 18 formed by several thin bars extending transversely to the blades and placed on the surface of the head on top of the cutting edges of the blades (4, 5, 6). Similar protection devices made of metal wire are known in the case of wet shavers and serve to limit the risk of cutting the skin. However, in the case of the second embodiment for which the first and last blades (4, 6) are supplied differently, the bars of the protection device 18 are made of insulating material, for example made of plastic, formed as one piece with the frame 9 of the head. Apart from protecting the skin, such a protection device made of nonconducting material may advantageously limit direct contact between the blades and the skin, and thus limit current transmission from the blades to the skin. However, the protection device could take a substantially different form, and in particular the form of a fine mesh in the case in which the shaving blades are set into motion by an electromechanical device, as is known in the case of dry shavers.

During shaving, the operating principle and the use of the shaving device are substantially the same whether the shaving head 3 is produced according to the first embodiment or the second embodiment.

To shave, the user actuates the control button 26 so that the current source 20 supplies at least one of the shaving blades (4, 5, 6). If the shaving device 1 is of the dry shaver type, as shown by way of example, the user may have applied beforehand a shaving product, such as a foam or a gel, to a defined area of the skin that has to be shaved.

Figure 3:
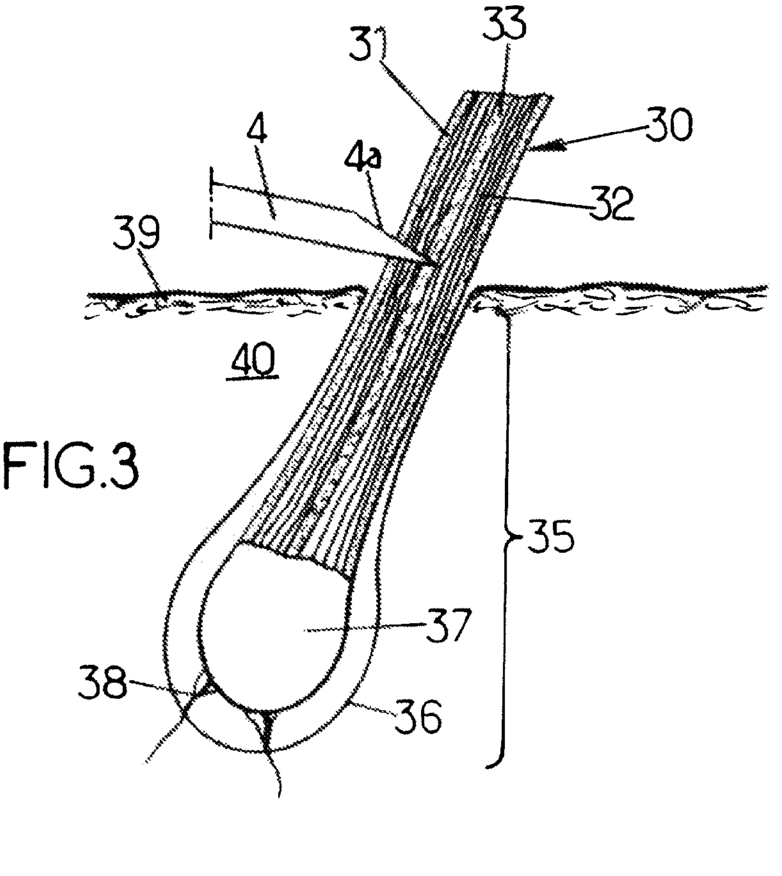
FIG. 3 is a diagram showing a hair being cut off by a blade.

The user then slides the shaving head 3 in contact with the skin in a usual movement and at a usual speed. When an electrically supplied blade (4, 5, 6; 4) encounters a hair 30, as shown schematically in FIG. 3, the cutting edge 4a of the blade passes through the cuticle 31 of the hair 30 and penetrates into the fibrous cortex 32, and then into the medulla 33 located at the center, while carrying out a pull-out action on the hair. It then appears that the electric current supplying the blade 4 is transmitted particularly well to the root 35 of the hair and especially to the bulb 36, the follicle 37 and the pupillae 38. Although the hair essentially consists of a material of low conductivity and that the outer sheath formed by the cuticle 31 is insulating, it is supposed that the fibrous nature promotes the flow of electricity into the hair along the direction of the fibers. In addition, owing to the pull-out effect, the contact time during which the blade 4 is in contact with the hair is increased compared with the contact time when the blade 4 is simply slid over the skin.

This may be put to particularly good use thanks to the invention for producing an electrolysis effect at the hair root 35, which effect is known per se but hitherto used for hair removal, that is to say sufficiently extensive destruction of the follicle 37 so that the hair falls out.

However, by transmitting the current via the cortex 32 and the medulla 33 of the hair, and not through the dermis 40 or onto the outer surface of the cuticle 31, the current flows predominantly as far as the follicle 37. The follicle 37 then acts as cathode, thereby promoting very localized production of NaOH at the bulb 36.

Consequently, the current source 20 is designed to deliver to the electrically supplied blade or blades (4, 5, 6; 4) a current and a voltage suitable for generating an electrolysis effect. As an indication, the voltage may be of the order of a few tens of volts and the maximum current delivered is of the order of a few milliamps. Contrary to what might be expected, it turns out that even if the time during which the blade is in contact with the cortex of the hair is very short, this duration is sufficient to cause an electrolysis effect, resulting in sufficient deterioration of the bulb 36 and the follicle 37 so that, after repeated use of the shaving device 1, it may be seen that hair regrowth has been slowed down.

Of course, this electrolysis effect when cutting a hair may be enhanced by the current transmitted by the blade 4 or the blades 4, 5, 6 owing to the contact with the skin, which current flows through the epidermis 39 and the dermis 40 until reaching the hair root 35. Likewise, the fact of providing additional conducting members, such as the lubricating strip 11 of the first embodiment or the stretching strip 16 of the second embodiment, is advantageous for enhancing the electrolysis effect.

However, it should be noted that transmission of the current through the dermis 40 may be painful because of the nerve receptors present therein. The voltage and the current that can be transmitted in this way are therefore limited. According to an additional feature of the invention, provision is made for the current transmitted to the roots via the hairs to have different characteristic from the current transmitted specifically by the skin using additional members (11; 16). It thus appears possible to optimize the amount of current transmitted to the hair roots with respect to skin sensitivity. This may be accomplished by designing the control module 23 of the current source 20 so that the first current output terminal 24a is capable of delivering electric power above that of the second terminal 24b, at least at discrete points when cutting one or more hairs, given that the blades act simultaneously over an extended region of the skin. This point electric power may be above the average power regulated and delivered by the control module 23 to the second output terminal 24b, while still maintaining a low risk of causing pain, since this power is essentially transmitted via the interior of the hair.

The current generating the electrolysis effect is returned via the shaving device itself, for effective and uniform circulation. This return to the terminal 25 of the current source takes place via a return line 15 and thanks to the contact made by one or both elements provided for this purpose, namely a conducting return member for the current coming into contact with the user, such as for example the contact element 7 of the gripping part of the handle. However, a device with no conducting current return member, which for example would have the advantage of providing a grounding function when the device is used beneath a shower, would not be outside the scope of the invention.

In the embodiments shown, the current source 20 delivers a DC current with a negative voltage at the terminals (24*a*, 24*b*) and a positive voltage at the terminal 25. However, any type of current capable of generating an electrolysis effect may be delivered by the source 20.

Thanks to the invention, what is obtained is a shaving device that can be used in the normal manner by the user and which, despite the short term in which it is in contact with the skin, causes electrolysis that has a significant effect on hair regrowth, at least after repeated use.

In particular, one of the advantages of the shaving device is that it makes it possible, at the same time, for the cutting edge of the blade (4, 5, 6), on the one hand, to pull on the hair and cut it and, on the other hand, to transmit an electrolysis current. The time during which the hair is being pulled and the cutting time therefore add together to result in a hair contact time during which the desired electrolysis effect occurs.

The negative current is delivered from the cutting edge (connected to the negative pole) and transmitted to the follicle 37, which constitutes the cathode, and therefore delivers a reduction current for generating an ionic compound that impairs the root of the hair in contact with the cutting edge. The current is for example returned via the handle held by the user, or a similar gripping member, away from the blades (4, 5, 6). The cutting edge of the blade 4 constitutes a surface with a small area of contact with the user. Conversely, the current return member 7 of the handle constitutes a surface with a much more extensive area, as may be seen in FIG. 1. The anode is formed by this current return member 7 having a very much larger area than the blade in contact with the skin, more than 1 $cm^2$ as opposed to a few $mm^2$ at most. The electrolytic action will thus be more diffuse at the anode, or even non-existing, because the current density is too low.

Of course, the embodiments described above are in no way limiting. The features of the two embodiments of the shaving head 3 may be interchanged or combined and, as indicated above, the application of the invention is not limited to three blades, or even to a wet shaver.

The invention claimed is:

1. A shaving device comprising:

a handle;

a shaving head intended to be moved in contact with the skin, wherein the shaving head comprises at least one blade made of conducting material, each blade having at a free end a single cutting edge suitable for cutting hairs;

a current source for supplying electrical current to said at least one blade, the current source being suitable for transmitting a current to generate an electrolysis effect at the root of a hair, at least while the hair is being cut by the blade; and a conducting current return member designed to come into contact with the skin during shaving, in a region different from the region to be shaved and connected to the current source in order to provide the current return back to the current source, wherein the conducting current return member is a gripping member for controlling movement of the shaving head, the gripping member being a part of the handle so as to be in contact with one's hand during use; and wherein the current source includes a negative terminal connected to the at least one blade and a positive terminal connected to the conducting current return member.

2. The shaving device of claim 1, wherein the current return member has an area intended to come into contact with the user that is greater than the area of the at least one blade capable of coming into contact with the region to be shaved.

3. The shaving device of claim 1, wherein the shaving head comprises a plurality of blades, wherein all the blades are capable of being electrically supplied in order to transmit an electrolysis current.

4. The shaving device of claim 1, wherein a skin protection device is placed at least partly on the cutting edge of the at least one blade, the protection device being made of non-conducting material.

5. The shaving device of claim 1, wherein an additional conducting current transmission member is placed on the shaving head so as to come into contact with the skin before the at least one blade has passed, and is supplied so as to transmit an electrolysis current to the root of a hair.

6. The shaving device of claim 5, wherein the additional current transmission member is a skin-stretching strip placed in front of the at least one blade.

7. The shaving device of claim 5, wherein the current source is suitable for transmitting electric currents of different characteristics to the at least one blade and to the additional transmission member.

8. The shaving device of claim 7, wherein the electric power transmitted by the at least one blade when cutting a hair is greater than the average power transmitted by the additional transmission member.

9. A shaving device comprising:

a handle;

a shaving head intended to be moved in contact with the skin, wherein the shaving head comprises at least two plate-like blades made of conducting material and having a cutting edge suitable for cutting hairs, the cutting edges of the blades being rectilinear and parallel;

a current source for supplying electrical current to said blades, the current source being suitable for transmitting a current to generate an electrolysis effect at the root of a hair, at least while the hair is being cut by one of said blades; and a conducting current return member designed to come into contact with the skin during shaving, in a region different from the region to be shaved and connected to the current source in order to provide the current return back to the current source, wherein the conducting current return member is a gripping member for controlling movement of said shaving head, said gripping member being a part of the handle so as to be in contact with one's hand during use; and wherein the current source includes a negative terminal connected to said blades and a positive terminal connected to the conducting current return member.

* * * * *